Oct. 9, 1962 M. A. THOMSON Plant Pat. 2,180
PEACH TREE
Filed March 6, 1961
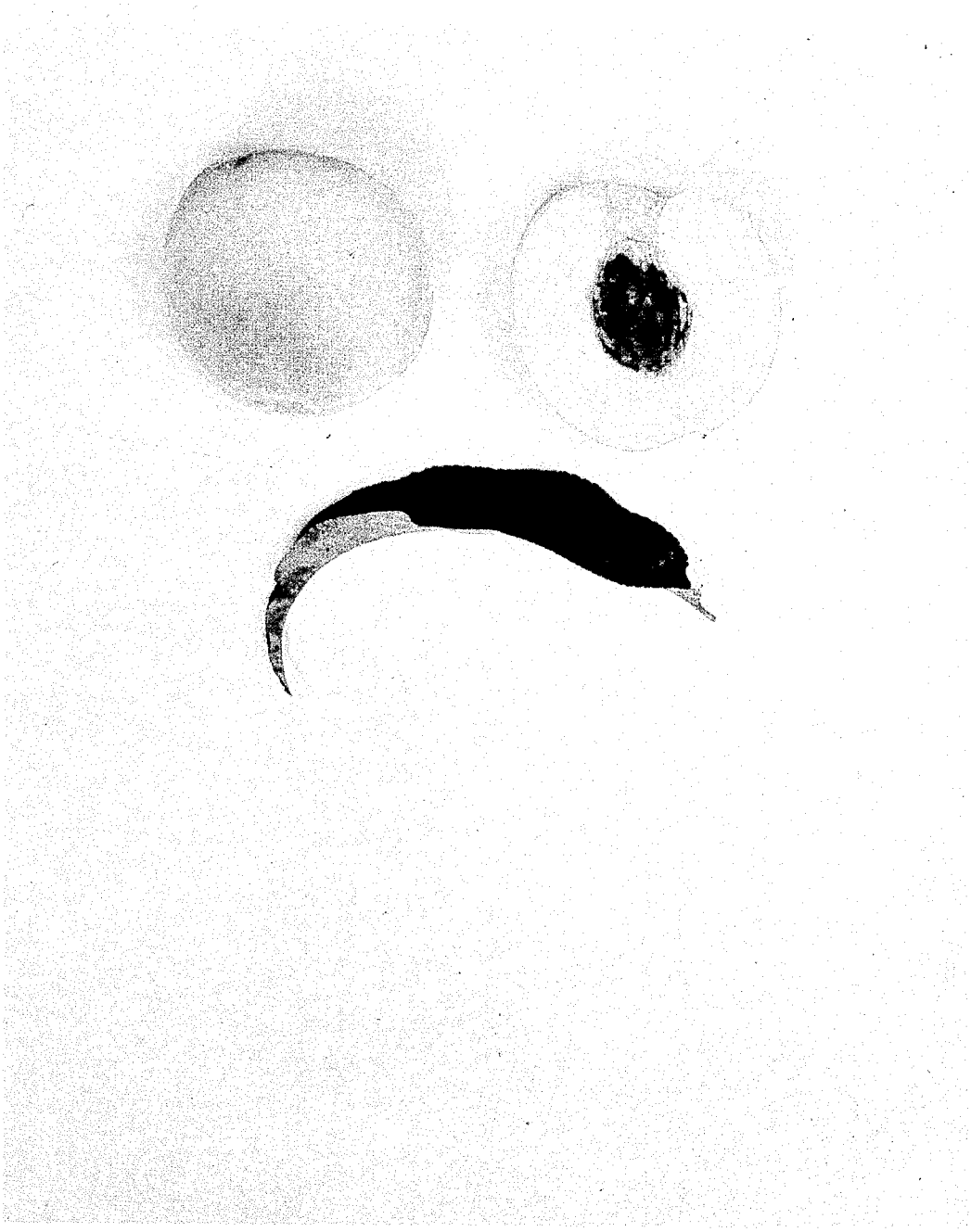
INVENTOR.
MORRIS A. THOMSON
Lyon & Lyon
ATTORNEYS.

United States Patent Office

Plant Pat. 2,180
Patented Oct. 9, 1962

2,180
PEACH TREE

Morris A. Thomson, Toppenish, Wash., assignor to California Packing Corporation, San Francisco, Calif., a corporation of California Filed Mar. 6, 1961, Ser. No. 93,821
1 Claim. (Cl. 47—62)

My present discovery is a new and improved variety of peach tree producing a fine quality of freestone fruit of the type used for canning. The tree has as its parentage the J. H. Hale unpatented crossed with the Halehaven unpatented.

The peach tree has been asexually reproduced by budding at farms located at Toppenish, Washington.

The peach tree has many desirable features including an extremely early ripening one to one and one half weeks earlier than the Halehaven and three and one half weeks before the J. H. Hale. The fruit is superior in flavor, texture and appearance to its parents and in quality is equal to, if not superior to the Elberta unpatented, although ripening some four weeks before the Elberta.

In the following detailed description color plate designations refer to the color plates of Maerz, A., and Paul, M. Rea, "A Dictionary of Color," McGraw Hill Book Co., New York, 1930.

*The Plant*

Growth: Medium in vigor, less than the Halehaven, but more than the J. H. Hale, with upright and spreading growth.

Bearing habits: Productive. Bore fruit during its third year in the field. Produces many fruit buds and sets heavy crop.

Leaves: The leaves are medium to large in size, generally 1¾ inches wide and from 5½ to 6¾ inches long. They are obovate-lanceolate in shape, having an obtuse base angle and a sharply acute apex angle with the leaf blade having a tendency to be slightly folded up. It is medium thick and leathery. The upper surface is a moderate olive green (Plate 23, C–12), fairly smooth, with terminal leaves being somewhat rugose. The lower surface is a grayish green (Plate 22, D–4) with very sparse fine pubescence along midrib. The midrib is prominent and slightly pinched. The veins are random in arrangement more than alternate. The margin of the leaf is finely serrate and shallow with the teeth of the serrated margin tipped with reddish-brown (Plate 8, L–5) glands.

Petiole: Generally ½ inch in lenth.

Glands: The number varies from 2 to 6 with 3 being the usual number. They are reniform in shape, medium in size, yellowish green (Plate 18, L–6) in color, and alternate more than opposite in position. Located principally on petiole within one centimeter of the leaf blade and on the edge of the leaf blade above the petiole.

*The Flower*

Bloom: Large showy blossom. This variety is self-fertile. Blooms one day earlier than Elberta.

Petals: Light pink (Plate 1, C–3) in color with a few flowers having almost white petals. Round in shape with a tendency toward being oval, smooth edges, somewhat cupped. Large petals 37/64 inch in width and 39/64 inch in length.

Stamens: Another color is yellow (Plate 18, L–1), and reddish (Plate 6, K–3) in color before blossoms open. Filaments are shorter than the petals averaging 33/64 inch in length.

Pistils: About 36/64 inch long, pubescent at ovary, greater in height than stamens next to pistil, but approximate height of stamens in outer whorl. Stigma a yellow green color (Plate 17, L–6).

Pedicel: About 1/16 inch in length, almost sessile, glabrous and green in color (Plate 18, I–7).

Calyx tube: Green (Plate 18, I–7) at base with reddish (Plate 6, K–3) color on sides, glabrous, orange (Plate 3, C–12) color on inside, medium in size, measuring 17/64 inch in diameter.

Sepals: Medium long, 15/64 inch in length, erect at 30° angle, glabrous within, and pubescent without, smooth edges.

*The Fruit*

Appearance: Produces a very attractive large sized fruit covered with a bright red blush (Plate 4, L–6) with a yellow ground color (Plate 10, L–6). This bright red blush will completely cover the fruit where it is exposed to the sun. The red coloring of the blush does not extend into the flesh. Fruit size two and a half to three inches with proper pruning and thinning.

Shape: A longitudinal section through the fruit will show it to be oblate in shape tending to roundness. The base end of the fruit is flattened, but the apex end is more rounded with the point being very slightly depressed. The point is a very inconspicuous feature. A transverse section of the fruit will show it to be elliptical in shape.

Pit cavity: Very little red (Plate 4, A–6) in the fresh fruit, but following processing this red completely disappears.

Flesh color: Yellow (Plate 10, L–6) similar to that of J. H. Hale.

Flesh adhesion: Free.

Flesh type: Medium firmness with melting flesh, fine texture, juicy.

Fresh fruit quality: Superior to either Redhaven unpatented or Triogem unpatented, two well known early varieties than ripen in approximately the same season as this variety.

Maturity: The fruit is firm ripe in one hundred and twenty six days from full bloom. Elberta reaches a comparable maturity in one hundred and fifty-four days from full bloom. The fruit clings well to the tree at harvest time and does not drop off as Elberta.

Skin: The amount of pubescence is light (short and rather thin). The peel is medium in thickness and separates very easily from the flesh at cannery ripeness.

Processed Fruit Quality:

*Color.*—Bright uniform yellow (Plate 9, L–6) of high intensity with a clear pit cavity. This clear pit cavity color is a desirable characteristic generally not found in commercially canned freestone varieties.

*Texture.* — Mellow fine texture with an absence of stringiness, but with sufficient firmness so that the peach half retains its shape during processing.

*Flavor.*—A delicate high peach flavor with a pleasing aroma. It falls in the medium range in acid and tannin. The combination of these factors results in this peach having a very high dessert quality.

Stone: Medium in size; obovate in form. The base angle of the stone is medium and angle at the apex is wide. The surface markings consist of numerous shallow grooves radiating from the base. Beyond these grooves are deep pits and chains of pits which become deep grooves across the body of the peach stone. The surface markings closely resemble those of the Late Crawford unpatented variety. The dorsal suture or ridge is medium in height and width with deep line markings. The ventral suture is medium in height. Rustic brown (Plate 7, H–11) in color with red staining (Plate 4, A–6) on surface.

Having thus disclosed my discovery, I claim:

The new and distinct variety of peach tree, substantially as herein shown and described, characterized by its early and prolific production of fruit, having very little red in the pit cavity which disappears upon processing, and which upon processing, prodluces a delicate high flavored peach.

No references cited.